(12) United States Patent
Gerber et al.

(10) Patent No.: US 7,682,355 B2
(45) Date of Patent: Mar. 23, 2010

(54) REFINED INFECTION MONITORING

(75) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/737,176

(22) Filed: Apr. 19, 2007

(65) Prior Publication Data

US 2008/0262379 A1 Oct. 23, 2008

(51) Int. Cl.
*A61K 9/22* (2006.01)
(52) U.S. Cl. .................. 604/891.1; 604/65; 604/66; 604/502; 604/503
(58) Field of Classification Search ........... 604/891.1, 604/65, 890.1, 31, 502–505, 66, 67; 600/300, 600/549; 607/6
See application file for complete search history.

(56) References Cited

U.S. PATENT DOCUMENTS

| | | | |
|---|---|---|---|
| 4,082,097 A * | 4/1978 | Mann et al. ............. | 607/33 |
| 5,029,582 A | 7/1991 | Lekholm | |
| 5,181,905 A | 1/1993 | Flam | |
| 5,476,485 A | 12/1995 | Weinberg | |
| 5,546,955 A | 8/1996 | Wilk | |
| 5,807,270 A | 9/1998 | Williams | |
| 5,820,263 A | 10/1998 | Ciobanu | |
| 6,016,447 A * | 1/2000 | Juran et al. ............. | 607/27 |
| 6,113,539 A | 9/2000 | Ridenour | |
| 6,135,968 A | 10/2000 | Brounstein | |
| 6,248,080 B1 * | 6/2001 | Miesel et al. ........... | 600/561 |
| 6,282,444 B1 | 8/2001 | Kroll | |
| 6,356,774 B1 | 3/2002 | Bernstein | |
| 6,558,351 B1 | 5/2003 | Steil | |
| 6,963,772 B2 | 11/2005 | Bloom | |
| 6,970,741 B1 | 11/2005 | Whitehurst | |
| 7,049,824 B2 | 5/2006 | Shabino | |
| 7,171,252 B1 * | 1/2007 | Scarantino et al. ........ | 600/345 |
| 2002/0042596 A1 | 4/2002 | Hartlaub | |

(Continued)

FOREIGN PATENT DOCUMENTS

DE 10150343 A1 4/2003

(Continued)

OTHER PUBLICATIONS

PCT International Search Report dated Nov. 19, 2007.

(Continued)

*Primary Examiner*—Kevin C Sirmons
*Assistant Examiner*—Deanna K Hall
(74) *Attorney, Agent, or Firm*—Campbell Nelson Whipps, LLC

(57) ABSTRACT

A method for monitoring infection in proximity to an implanted medical device includes monitoring an indicator of infection in proximity to the device and determining whether a value associated the indicator of infection crosses a first threshold indicative of infection. The method further includes detecting an event associated with the device. The event is capable of affecting the indicator of infection. The method also includes determining whether the value associated with the indicator of infection crosses a second threshold indicative of infection if the event is detected. The method may further include issuing an alert if (i) the first threshold is crossed and the event is not detected, or (ii) the second threshold is crossed and the event is detected.

6 Claims, 8 Drawing Sheets

U.S. PATENT DOCUMENTS

| | | |
|---|---|---|
| 2003/0032892 A1 | 2/2003 | Erlach |
| 2003/0194752 A1 | 10/2003 | Anderson |
| 2003/0199783 A1 | 10/2003 | Bloom |
| 2003/0216677 A1 | 11/2003 | Pan |
| 2004/0066313 A1 | 4/2004 | Ong |
| 2004/0236192 A1 | 11/2004 | Necola Shehada |
| 2005/0012610 A1 | 1/2005 | Liao |
| 2005/0090761 A1 | 4/2005 | Carney |
| 2005/0096584 A1 | 5/2005 | Ferek-Petric |
| 2005/0171580 A1* | 8/2005 | MacDonald .............. 607/61 |
| 2006/0047218 A1 | 3/2006 | Bloom |
| 2006/0062852 A1 | 3/2006 | Holmes |
| 2006/0079793 A1 | 4/2006 | Mann |
| 2006/0149331 A1 | 7/2006 | Mann |
| 2006/0224088 A1 | 10/2006 | Roche |
| 2006/0271108 A1 | 11/2006 | Libbus |
| 2008/0064980 A1 | 3/2008 | Lee |

FOREIGN PATENT DOCUMENTS

| | | |
|---|---|---|
| GB | 2 405 203 | 2/2005 |
| WO | WO 02/068049 | 9/2002 |
| WO | WO 2005/000091 | 1/2005 |
| WO | WO 2005/000160 | 1/2005 |
| WO | WO 2006/013585 | 2/2006 |
| WO | WO 2006/048554 | 5/2006 |
| WO | WO 2007/028035 | 3/2007 |

OTHER PUBLICATIONS

PCT International Search Report dated Oct. 10, 2007.
U.S. Appl. No. 11/737,180, filed Apr. 19, 2007, Gerber.
U.S. Appl. No. 11/737,173, filed Apr. 19, 2007, Gerber.
U.S. Appl. No. 11/737,181, filed Apr. 19, 2007, Gerber.
U.S. Appl. No. 11/737,179, filed Apr. 19, 2007, Gerber.
U.S. Appl. No. 11/737,171, filed Apr. 19, 2007, Gerber.
U.S. Appl. No. 11/737,170, filed Apr. 19, 2007, Gerber.
U.S. Appl. No. 11/737,169, filed Apr. 19, 2007, Gerber.
Robicsek, F., et al., The value of thermography in the early diagnosis of postoperative sternal wound infections. Thoracic & Cardiovascular Surgeon, 1984. 32(4): p. 260-5.
Saxena, A.K., et al., Thermography of Clostridium perfringens infection in childhood. Pediatric Surgery International, 1999. 15(1): p. 75-6.
Waterman, N.G., L. Goldberg, and T. Appel, Tissue temperatures in localized pyogenic infections. American Journal of Surgery, 1969. 118(1): p. 31-5.
PCT International Search Report dated Dec. 5, 2007.
U.S. Appl. No. 60/825,101, filed Sep. 2006, Lee.

* cited by examiner

REFINED INFECTION MONITORING

FIELD

This disclosure relates, inter alia, to implantable medical devices. More particularly, it relates to systems, devices and methods for monitoring infection in proximity to medical devices implanted in patients.

BACKGROUND

Infection associated with implantation of medical devices is a serious health and economic concern. Today, infections associated with implanted medical devices are not very common due to care and precautions taken during surgical implantation of the devices. However, when infection associated with an implanted medical device (IMD) does occur, explanting the device is often the only appropriate course of action.

For IMDs having a battery powered component, such as implantable cardiac pacemakers, cardioverter/defibrillators having pacing capabilities, other electrical stimulators including spinal cord, deep brain, nerve, and muscle stimulators, infusion devices, cardiac and other physiologic monitors, cochlear implants, etc., the battery powered component is typically enclosed in a housing that is implanted subcutaneously at a surgically prepared site, referred to as a "pocket". Associated devices, such as elongated medical electrical leads or drug delivery catheters, extend from the pocket to other subcutaneous sites or deeper into the body to organs or other implantation sites.

Surgical preparation and implantation are conducted in a sterile field, and the IMD components are packaged in sterile containers or sterilized prior to introduction into the sterile field. However, despite these precautions, there always is a risk of introduction of microbes into the pocket. Surgeons therefore typically apply disinfectant or antiseptic agents to the skin at the surgical site prior to surgery, directly to the site before the incision is closed, and prescribe oral antibiotics for the patient to ingest during recovery.

Despite these precautions, infections do occur. In addition, once the pocket becomes infected, the infection can migrate along the lead or catheter to the heart, brain, spinal canal or other location in which the lead or catheter is implanted. Such a migrating infection can become intractable and life-threatening, requiring removal of the IMD in the pocket and associated devices, such as leads and catheters. Removal of a chronically implanted lead or catheter can be difficult and dangerous. Accordingly, aggressive systemic drug treatment is prescribed to treat such infections. However, early detection of infection associated with implanted medical devices may allow for earlier intervention, resulting in fewer device explants.

Monitoring of infection through the use of sensors, such as temperature sensors, that can provide information indicative of infection, has been proposed. However, various events associated with an implanted device may affect the sensed information and lead to an incorrect determination as to whether an infection is present in proximity to the implanted device. For example, recharging of the device may lead to increased temperature in proximity to the device, which may lead to a false positive determination that the increased temperature is due to an infection.

SUMMARY

The present disclosure describes, inter alia, systems, devices and methods that can be used to monitor an infection in proximity to an implanted medical device and which take into account events that may affect the monitored indicator when making a determination as to whether an infection is in proximity to the implanted device.

In various embodiments, a method for monitoring an infection in proximity to an implanted medical device is described. The method includes monitoring an indicator of infection in proximity to the device and determining whether a value associated the indicator of infection crosses a first threshold indicative of infection. The method further includes detecting an event associated with the device, the event capable of affecting the indicator of infection and determining whether the value associated with the indicator of infection crosses a second threshold indicative of infection if the event is detected. The method may further include issuing an alert if (i) the first threshold is crossed and the event is not detected, or (ii) the second threshold is crossed and the event is detected. Devices and systems capable of carrying out the method are also described herein.

By providing devices, systems and methods that account for events associated with an implantable device in determining whether an infection may be present in proximity to the device, improved accuracy of such determinations may be made. Such improved accuracy will provide the patient in which the device is implanted and their health care providers with better information regarding the likelihood of an infection. These and other advantages will be readily understood from the following detailed descriptions when read in conjunction with the accompanying drawings.

Figure 1:
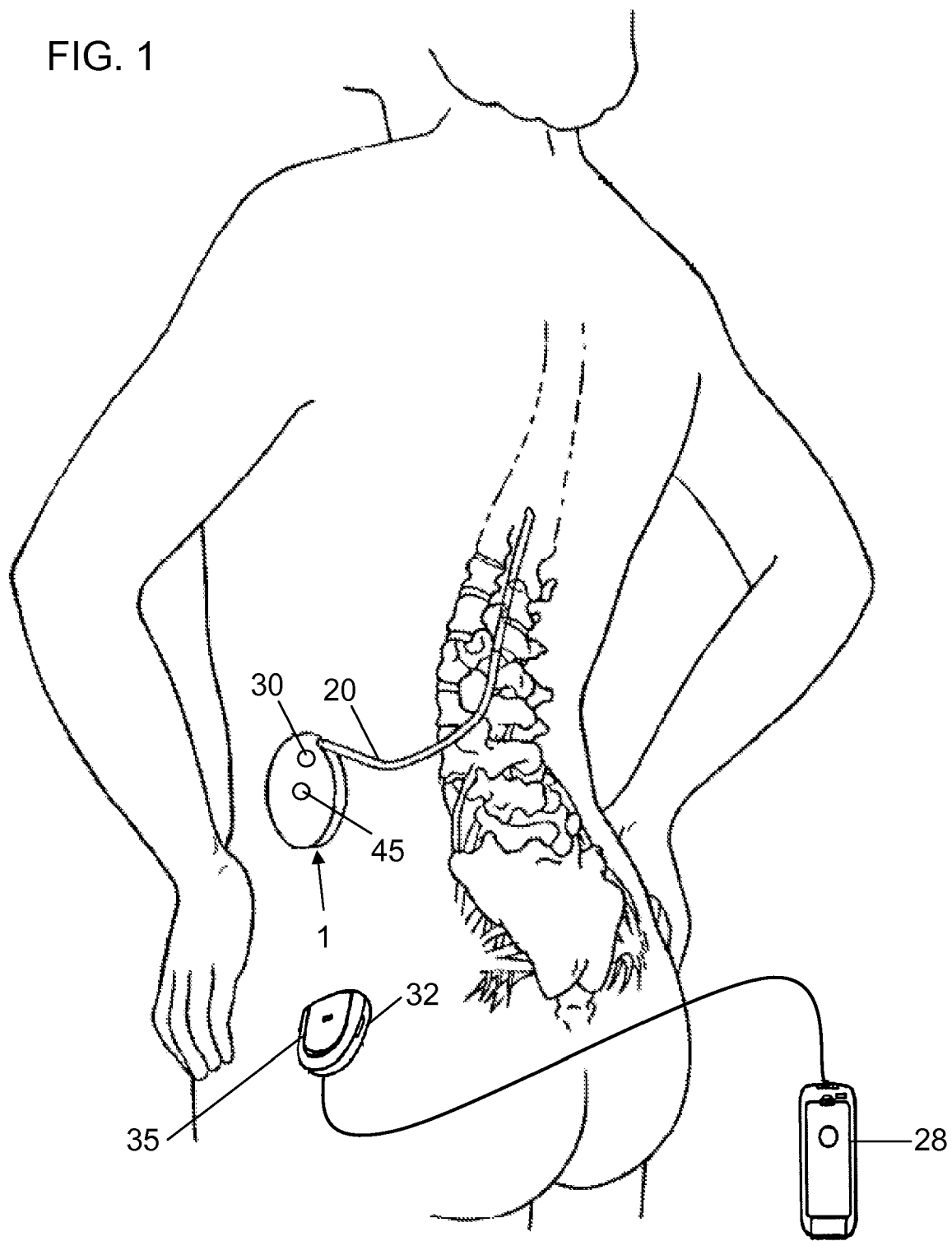
FIG. 1 is a diagrammatic representation of a perspective view of an environment of an implantable infusion system implanted in a patient.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "active implantable medical device" means an implantable medical device that includes a power source to deliver therapy to a patient. Non-limiting examples of active implantable medical devices include implantable infusion devices and implantable electrical signal generators, such as cardiac defibrillators, pacemakers, neurostimulators, gastric stimulators, and cochlear implants. Active implantable medical devices typically are used in conjunction with associated implantable medical devices, such as catheters or leads.

As used herein, "crosses a threshold", or the like, means meets or exceeds a threshold. It will be understood that a decrease in a value may "exceed" a threshold. For example, if a threshold is a pH of less than 6.5, a pH of 6.4 exceeds the threshold. Similarly, if a threshold is a 10% deviation from a mean value, an 11% negative deviation exceeds the threshold.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

The present disclosure describes, inter alia, systems, devices and methods that can be used to monitor an infection in proximity to an implanted medical device and which take into account events that may affect the monitored indicator when making a determination as to whether an infection is in proximity to the implanted device. The methods, systems and devices monitor an indicator of infection and determine whether the indicator crosses a threshold indicative of infection. If an event that may affect the indicator is detected, the threshold may be modified to account for the event. Thus, more accurate determinations as to whether an infection is in proximity to an implanted device may be made.

The teachings described herein may be employed in conjunction with nearly any implantable medical device, including monitoring devices. Examples of some types of devices that are likely to experience events that may affect an indicator of infection include devices that may transmit or receive information and devices that may be recharged.

Figure 2:
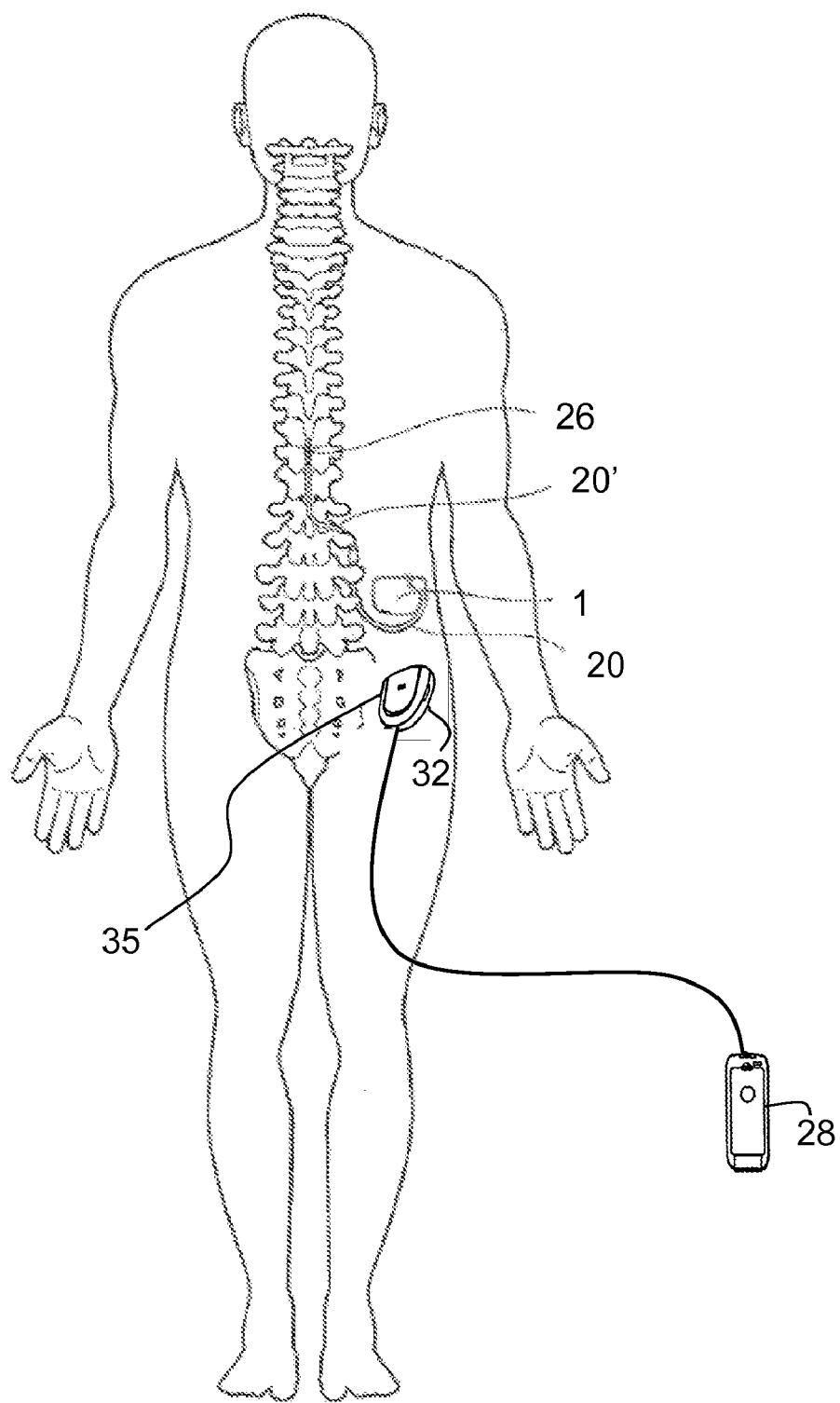
FIG. 2 is a diagrammatic representation of a perspective view of an environment of an implantable electrical signal generator system implanted in a patient

Referring to FIGS. 1 and 2, general representative environments for implanting active medical devices 1 and associated devices 20 are shown. Active medical device 1 is subcutaneously implanted in an abdominal region of a patient. A distal portion of associated device 20 is intrathecally inserted into the patient's spinal canal through a lumbar puncture and advanced rostrally to a desired location (FIG. 1) or epidurally placed along a suitable location of spinal cord (FIG. 2). Proximal end of associated device 20 is tunneled subcutaneously to location of active device 1, where it may be connected to active device 1. While distal portion of associated device 20 is shown in FIGS. 1 and 2 as being located in or on spinal cord, it will be understood that associated device 20 may be placed at any location in patient for which it is desirable to administer therapy generated or delivered by active medical device 1.

In the embodiment shown in FIG. 1, active implantable device 1 is an infusion device, and associated device 20 is a catheter. Catheter 20 is typically a flexible tube with a lumen running from the proximal end of catheter 20 to one or more delivery regions that are typically located at the distal portion of catheter 20. Proximal portion of catheter 20 is connected to infusion device 20. Distal portion of catheter 20 is positioned at a target location in the patient to deliver fluid containing therapeutic agent from infusion device 1 to patient through a delivery region of catheter 20. Infusion device 1, such as Medtronic Inc.'s SynchroMed™ II implantable programmable pump system, includes a reservoir (not shown) for housing a therapeutic substance and a refill port 45 in fluid communication with reservoir. The reservoir may be refilled by percutaneously inserting a needle (not shown) into patient such that needle enters refill port 45, and fluid containing therapeutic substance may be delivered into reservoir from needle via refill port 45. Infusion device 1 shown in FIG. 1 also includes a catheter access port 30 that is in fluid communication with the catheter 20. Fluid may be injected into or withdrawn from patient through catheter 20 via catheter access port 30 by percutaneously inserting a needle into access port 30. Each entry of needle across patient's skin to gain access refill port 45 or access port 30 results in the possibility of infection in proximity to the active medical device 1.

In the embodiment shown in FIG. 2, active implantable device 1 is an electrical signal generator, such as Medtronic Inc.'s Restore™ Advanced implantable neurostimulator, and associated devices 20, 20' are a lead extension 20 and lead 20'. Lead 20' includes one or more electrical contacts (not shown) on its proximal end portion and one or more electrodes on its distal end portion 26. The contacts and electrodes are electrically coupled via wires running through lead 20'. Electrical signals generated by the signal generator 1 may be delivered to lead 20 through the contacts and then to the patient through the electrodes. As shown in FIG. 2, lead 20' may be connected to signal generator 1 through a lead extension 20. Extension 20 includes one or more contacts at the proximal and distal end portions that are electrically coupled through wires running through extension 20. Of course it will be understood that with some systems lead 20' may be directly connected to electrical signal generator 1 without use of a lead extension 20. It will be further understood that more than one lead 20' or lead extension 20 may be employed per signal generator 1.

While FIGS. 1 and 2 depict systems including infusion devices and electrical signal generators, it will be understood that the teachings described herein may be applicable to virtually any known or future developed active implantable medical device and that virtually any non-active implantable medical device may be appropriately adapted and configured to perform according to the teachings provided herein. In addition, it will be understood that device 1 may be implanted in any medically acceptable location and need not be implanted in a patient's abdomen as shown in FIGS. 1 and 2.

In various embodiments, implantable medical device 1 is rechargeable. As shown in FIGS. 1 and 2, a recharge head 35 containing a primary coil 32 may be operably coupled to a recharging device 28, which may be, for example, a physician or a patient programmer that has charging capacity. Recharging an implantable medical device 1 generally begins with placing a recharging head 35 containing a primary recharging coil 32 against the patient's skin near the proximal side of the medical device 1. Some rechargers 28 have an antenna locator that indicates when recharge head 35 is aligned closely enough with implanted medical device 1 for adequate inductive charge coupling. The recharge power transfer signal is typically a frequency that will penetrate transcutaneous to the location of implanted medical device 1 such as a frequency in the range from 5.0 KHz to 100 KHz. The power transfer signal is converted by implantable medical device 1 into regulated DC power that is used to charge a rechargeable power source. Telemetry can also be conducted between the recharger 28 and the implanted medical device 1 during recharging. Telemetry can be used to aid in aligning recharger 28 with the implanted medical device 1, and telemetry can be used to manage the recharging process. Telemetry is typically conducted at a frequency in the range from 150 KHz to 200 KHz using a medical device telemetry protocol, but may also include Bluetooth, 802.11, and Medical Implant Communication Service (MICS) frequency band communication. For telemetry, the recharger 28 and implanted medical device 1 typically have a separate telemetry coil. Although, the recharging coil can be multiplexed to also serve as a telemetry coil. Additional information regarding recharging and infection monitoring is provided in U.S. patent application Ser. No. 11/737,179, entitled "CONTROLLING TEMPERATURE DURING RECHARGE FOR TREATMENT OF A CONDITION", filed on even date herewith, naming Martin Gerber and John Rondoni as inventors, which application is hereby incorporated herein by reference to the extent that it does not conflict with the disclosure presented herein. Of course implantable medical device 1 need not be rechargeable for the teachings presented herein to apply.

Figure 3:
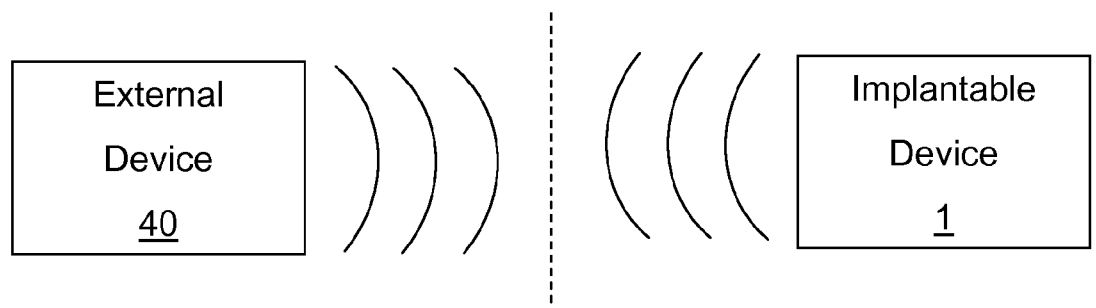
FIG. 3 is a diagrammatic representation of an external device in wireless communication with an implantable medical device.

Regardless of whether device 1 is rechargeable, in various embodiments, device 1 is able to communicate with an external device. Referring to FIG. 3, an external device 40 in wireless communication with implantable device 1 is shown. External device 40 may communicate with implantable device 1 through patient's skin, which is represented by the dashed line in FIG. 3. In various embodiments implantable device 1 carries out the various infection monitoring methods, or portions thereof, described herein. In some other embodiments the combination of implantable device 1 and external device 40 carry out the various infection monitoring methods, or portions thereof, described herein. In various embodiments, where implantable device 1 is a programmable device, external device 40 may be a programmer device, such as Medtronic Inc.'s N'Vision™ clinician programmer. Of course external device may be any device capable of wirelessly communicating with implantable device 1, such as a patient programmer, a computer, a personal data assistant, or the like. External device 40 and implantable device 1 may be capable of one-way (external device 40 to implantable device 1 or implantable device 1 to external device 40) or two-way communication.

Figure 4A:
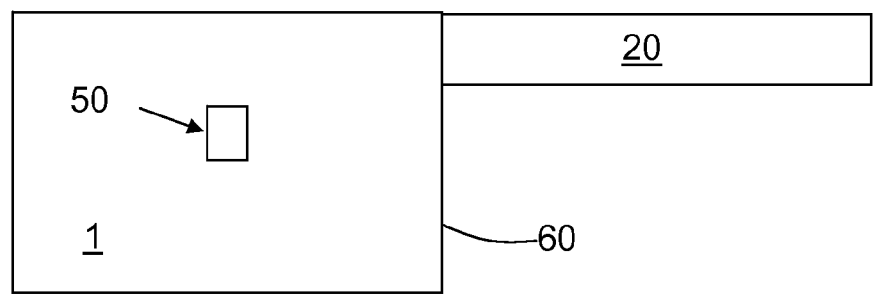
FIGS. 4A-B are a diagrammatic representation of a side view (A) and back view (B) of an implantable medical device system having sensor(s) in proximity to the implantable device.
Figure 4B:
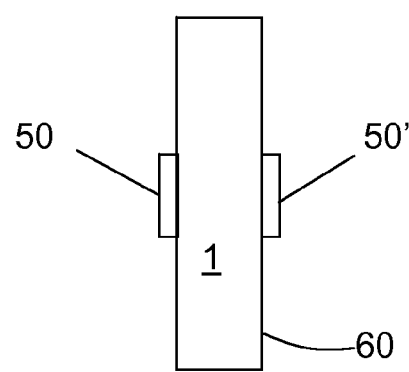

Referring to FIG. 4, sensor(s) 50, 50' associated with implantable active medical device 1 is shown. FIG. 4A is a side view of a representative active device 1 and associated device 20. FIG. 4B is a back view of a representative active device 1. One or more sensor 50, 50' may be located in proximity to device 1; e.g., disposed on, in, or near housing 60 of device 1. Sensor 50, 50' may be any device capable of detecting and transmitting information regarding an indicator of infection to device 1. If housing 60 is hermetically sealed, feedthroughs (not shown) may be used to provide electrical connectivity through housing 60 while maintaining the hermetic seal. While not shown, it will be understood that one or more sensor capable of detecting an indicator of infection may be located on, in, or about accessory device 20. Examples of physical or chemical stimuli that may serve as indicators of infection are temperature, impedance, pH, and biological markers of infection.

Changes in temperature in proximity to implanted device 1 may be used as an indicator of infection in proximity to device 1. The temperature of body tissue at a site of infection is generally greater than that of body tissue at a location removed from the site of infection. Accordingly, an increase in temperature in proximity to an implanted medical device 1 may serve as an indicator of infection. Any suitable sensor 50, 50' capable of detecting temperature or changes in temperature may be employed. For example, temperature sensor 50, 50' may include a thermocouple, a thermistor, a junction-based thermal sensor, a thermopile, a fiber optic detector, an acoustic temperature sensor, a quartz or other resonant temperature sensor, a thermo-mechanical temperature sensor, a thin film resistive element, or the like.

Changes in impedance of tissue in proximity to implanted device 1 may be used as an indicator of infection in proximity to device 1. For example, an increase in fluid in tissue is often observed at a site of an infection. Accordingly, a decrease in impedance of tissue in proximity may serve as an indicator of infection. In the case of impedance measurement, detection or monitoring, sensors 50, 50' are electrodes. Impedance may be measured between two electrodes. Current or voltage is applied between the electrodes with one electrode at any given time serving as a source and the other serving as a sink. In various embodiments, electrodes will be positioned at opposing surfaces of housing 60 of device 1. In other embodiments, one electrode may be located on accessory device 20, e.g. on a lead, and one may be located on housing of device 1. Alternatively or in addition, one electrode may be located on accessory device 20 and housing 60 of device 1 may serve as a return electrode in a manner similar to unipolar signal generators. Further, it will be understood that more than one electrode pair may be employed to monitor impedance.

In instances where device 1 is an electrical signal generator, the electrical components used for generating therapeutic electrical signals may also be used for generating signals for impedance monitoring. In instances where device 1 is not an electrical signal generator, e.g. device 1 is an infusion pump, components capable of generating appropriate electrical signals for testing impedance of body tissue may be incorporated into device 1. Any impedance detection components or circuitry may be employed. For example, an ohm meter or a wheatstone bridge design may be used to measure or detect changes in impedance or resistance. Examples of additional suitable components or circuitry are described in, for example, the following patents and applications assigned to Medtronic, Inc.: US 2006/0259079; US 2006/0036186; US 2004/0162591; US 2003/0176807; U.S. Pat. No. 5,876,353; U.S. Pat. No. 5,824,029; and U.S. Pat. No. 5,282,840.

Changes in pH in proximity to implanted device 1 may be used as an indicator of infection in proximity to device 1. As pH may serve as a general indicator of the state of a tissue, a change in pH may be indicative of infection. Accordingly, a sudden or gradual change in pH in proximity to an implanted medical device 1 may serve as an indicator of infection. Any suitable sensor 50, 50' capable of detecting pH or changes in pH may be employed.

Any biological markers of infection may be detected in accordance with the teachings presented herein. Non-limiting examples of biological markers of infection include viral, fungal, or bacterial proteins or nucleic acids or fragments thereof. As most infections associated with implantable medical devices appear to be due to infection due to *Staphlococcus aureus*, *Staphlococcus epidermis*, *Pseudomonus auruginosa* and *Candidia* Sp., detection of proteins, nucleic acids, or fragments thereof of such microorganisms may be beneficial. Alternatively, detection of indicators of an immune response may be detected. For example, an increase in a pro-inflammatory cytokine. Non-limiting examples of proinflammatory cytokines include tumor necrosis factor (TNF; also known as TNFα or cachectin), interleukin (IL)-1α, IL-1β, IL-2; IL-5, IL-6, IL-8, IL-15, IL-18, interferon γ (IFN-γ); platelet-activating factor (PAF), thromboxane; soluble adhesion molecules; vasoactive neuropeptides; phospholipase A2; plasminogen activator inhibitor (PAI-1); free radical generation; neopterin; CD14; prostacyclin; neutrophil elastase; protein kinase; monocyte chemotactic proteins 1 and 2 (MCP-1, MCP-2); macrophage migration inhibitory factor (MIF), high mobility group box protein 1 (HMGB-1), and other known factors. Indication of an immune response may also be detected by an decrease in an anti-inflammatory cytokine in proximity to device 1. Non-limiting examples of anti-inflammatory cytokines include IL-4, IL-10, IL-17, IL-13, IL-1α, and TNFα receptor. It will be recognized that some of proinflammatory cytokines may act as anti-inflammatory cytokines in certain circumstances, and vice-versa. Such cytokines are typically referred to as plieotropic cytokines. An immune response may also be detected by measuring changes (baseline versus after device implant or other event, a first point after device implant or other event versus a second point after device implant or other event, etc.) in the presence of other factors involved in an immune response. Non-limiting examples of such other factors include TGF, PDGF, VEGF, EGF, FGF, I-CAM, and nitric oxide. In addition, an immune response may be detected by changes in chemokines, such as 6cKine and MIP3beta, and chemokine receptors, including CCR7 receptor. Further, an immune response may be measured by changes in immune cell population (upregulated Langerhans cells, dendritic cells, lymphocytes), or immune cell surface co-stimulatory molecules (Major Histocompatibility, CD80, CD86, CD28, CD40). An immune response may also be detected by measuring changes in other factors involved in the inflammatory cascade, for example in the signal transduction cascades including factors such as NFκ-B, Egr-1, Smads, toll-like receptors, and MAP kinases. In addition, an immune response may be detected by a change in the presence of an exogenous antigen believed to have caused an inflammatory response, such as, e.g., a bacteria, a virus, or a fungus.

Any sensor capable of detecting such biological markers indicative of infection may be used. In various embodiments, a biosensor is used to detect the presence of a molecule in proximity to implanted device 1. Any known or future developed biosensor may be used. The biosensor may have, e.g., an enzyme, an antibody, a receptor, or the like operably coupled to, e.g., a suitable physical transducer capable of converting the biological signal into an electrical signal. In some situations, receptors or enzymes that reversibly bind the molecule being detected may be preferred. In various embodiments, sensor 50, 50' includes an electrode with an ion selective coating that is capable of directly transducing the amount of a particular substance. An example of this type of transducer is described in the paper "Multichannel semiconductor-based electrodes for in vivo electrochemical and electrophysiological studies in rat CNS" by Craig G. van Home, Spencer Bement, Barry J. Hoffer, and Greg A. Gerhardt, published in Neuroscience Letters, 120 (1990) 249-252. In various embodiments, sensor 50, 50' may be a sensor as described in, e.g., U.S. Pat. No. 5,978,702, entitled TECHNIQUES OF TREATING EPILEPSY BY BRAIN STIMULATION AND DRUG INFUSION or U.S. 2005/0209513, entitled COLLECTING SLEEP QUALITY INFORMATION VIA A MEDICAL DEVICE, filed Apr. 15, 2004, and published Sep. 22, 2005. Modifications of the teachings presented in the above-cited references may be made to account for one or more biological marker of infection.

For certain biological markers, e.g. proteins or nucleic acids or fragments thereof of microorganisms responsible for infection, merely the presence of such markers may be indicative of an infection. For other markers that may be present in a patient lacking an infection, e.g. cytokines and chemokines, increases or decreases in the levels of such markers may be indicative of an infection.

For the above-discussed indicators of infection or other indicator of infection, a determination of the presence of infection in proximity to implanted device 1 may be made in any suitable fashion. For example, a determination of infection may be made if a given indicator is detected at, above or below a predetermined threshold value. For example, if a temperature of 101° F. (38.3° C.) is detected, a determination may be made that an infection is present in proximity to implanted device 1. Alternatively or in addition, a determination of infection may be made if a given indicator is detected at, above or below a predetermined value for a predetermined period of time. For example, if a temperature of 100.5° F. (38.1° C.) or greater is detected for two hours or more is detected for two hours or more, a determination may be made that an infection is present in proximity to implanted device 1. Of course other types of trends in information regarding indicators of infection may be used advantageously to improve the accuracy of determinations of infections in proximity to an implanted medical device. Additional information regarding use of thresholds determining infection in proximity to an implantable medical device is provided in U.S. patent application Ser. No. 11/737,180, entitled "Indicator Metrics For Infection Monitoring", filed on even date herewith, naming Martin Gerber and John Rondoni as inventors, which application is hereby incorporated herein by reference in its entirety to the extent it does not conflict with the disclosure presented herein.

For the above-discussed indicators of infection or other indicator of infection, it may be desirable to compare levels of the indicators at a location in proximity to device 1 and at a location removed from device. Such comparisons may allow for a reduction in false positive detections. For example, elevation in temperature in proximity to device 1 may be due to localized infection or may be due to increased activity of the patient; increases in inflammatory cytokines in proximity to the device may be due to localized infection or a more general immune response; etc. By comparing the level of an indicator of infection in proximity to an implanted device to the level at a location removed from the device, a more accurate determination of whether an infection is present in proximity to the device may be made. Additional information regarding monitoring an indicator of infection at two locations is provided in U.S. patent application Ser. No. 11/737,171, entitled "Implantable Therapy Delivery System Having Multiple Temperature Sensors", filed on even date herewith, naming Martin Gerber and John Rondoni as inventors, which application is hereby incorporated herein by reference in its entirety to the extent it does not conflict with the disclosure presented herein.

Information regarding a first indicator of infection may be used to determine whether an infection is present in proximity to the implanted device 1. In various situations, it may be desirable to use one or more second indicators of infection to determine whether the indication based on the first indicator is accurate. Additional information regarding infection monitoring using two or more indicators of infection is provided in U.S. patent application Ser. No. 11/737,181, entitled "Multi-Parameter Infection Monitoring", filed on even date herewith, naming Martin Gerber and John Rondoni as inventors, which application is hereby incorporated herein by reference in its entirety to the extent it does not conflict with the disclosure presented herein.

Figure 5:
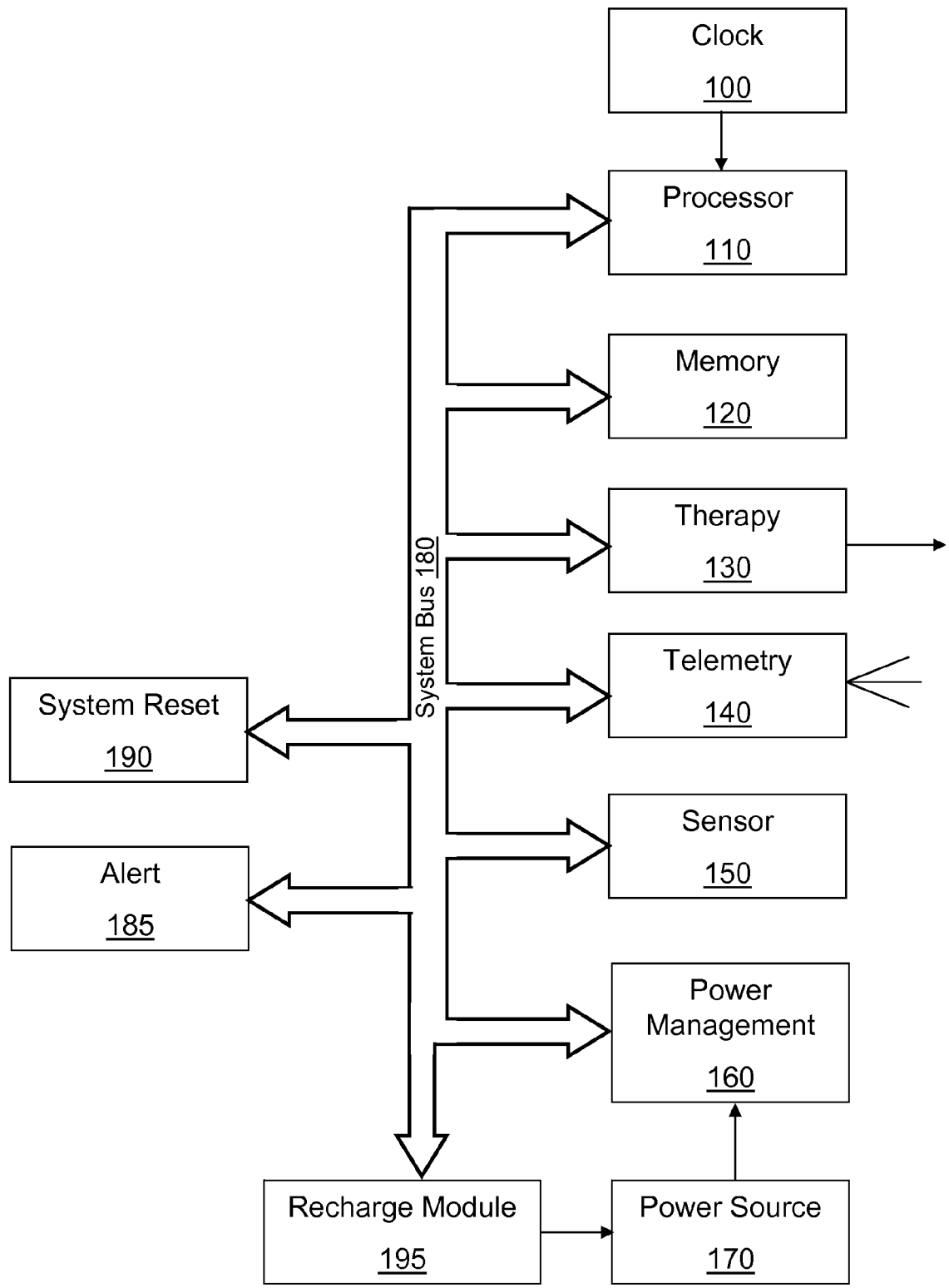
FIG. 5 is a schematic block diagram of representative components of a representative implantable medical device.

Referring to FIG. 5, some representative electronic components of an implantable medical device 1 according to various embodiments are shown in block form. Active implantable medical device 1 as depicted in the embodiment shown in FIG. 6 includes a clock 100, a processor 110, a memory 120, a therapy output or delivery component 130, a telemetry component 140, a sensor 150, a power management module 160, a power source 170, an alert module 185, a system reset module 190, and a recharge module 195. Other components of active implantable medical device 1 can include, e.g., a diagnostics module (not shown). All components except the power source 170 can be configured on one or more Application Specific Integrated Circuits (ASICs) or may be one or more discrete components, or a combination of both. Also, all components, except the clock and power source are connected to bi-directional data bus 180 that is non-multiplexed with separate address and data lines.

Processor 110 may be synchronous and typically operates on low power, such as Motorola 68HC11 synthesized core operating with a compatible instruction set. Clock 100 counts the number of seconds since a fixed date for date/time stamping of events and may be used for therapy control. Memory 120 includes memory sufficient for operation of device 1, such as volatile Random Access Memory (RAM) for example static RAM, nonvolatile Read Only Memory (ROM), Electrically Erasable Programmable Read Only Memory (EEPROM) for example Flash EEPROM, and register arrays configured on ASICs. Direct Memory Access (DMA) is available to selected modules such as telemetry module 140 or sensor module 150, so that the selected modules can request control of data bus 180 and write data directly to memory 120 bypassing processor 110. System Reset 190 controls operation of ASICs and modules during power-up of device 1, so ASICs and modules registers can be loaded and brought on-line in a stable condition.

Telemetry 140 module or other wireless module provides for communication between implantable device 1 and external device 40 such as a programmer. Communication may be bi-directional. Telemetry module 140 generally includes a telemetry antenna, a receiver, a transmitter, and a telemetry processor. Telemetry modules are generally known in the art and are further detailed in U.S. Pat. No. 5,752,977, entitled "Efficient High Data Rate Telemetry Format For Implanted Medical Device" issued to Grevious et al. (May 19, 1998). While module 140 is referred to herein as "telemetry" module, it will be understood that other forms of wireless communication may readily be substituted where appropriate for telemetry. Examples of forms of wireless communication include Bluetooth®, 802.11, and Medical Implant Communication Service (MICS) frequency band communication.

Therapy module 130 refers to components for carrying out the delivery or generation of therapeutic output to be delivered to a patient from active device 1. One of skill in the art will appreciate that the components may vary on a device-by-device basis and a therapy-by-therapy basis. For example, therapy module 130 may contain an oscillator if device 1 is an electrical signal generator and may contain a pumping mechanism if device 1 is an infusion device.

Sensor module 150 includes circuitry associated with one or more sensors 50, 50' and may include other components for transmitting sensed information from sensor 50, 50' to, e.g., processor 110 or memory 120. Sensor module 150 or other components of device 1 may include one or more analog to digital converters to convert analog signals generated by sensor 50 into digital signals usable by processor 110, as well as suitable filter and amplifier circuitry.

Alert module 185 may issue an alert, e.g. an audible alert or tactile alert, such as a vibration. An alert may be issued if information indicative of an infection is detected. The alert will serve to prompt the patient to seek medical attention.

It will be understood that the components described in FIGS. 1-5 and 7 are but examples of components that an implantable device 1 may have and that many other device or system configurations may be employed to carry out the methods described below. However, for the sake of convenience, the discussion that follows with regard to the methods illustrated in the flow diagrams of FIGS. 6 and 8-9 will refer to components as described with regard to FIGS. 1-5 and 7.

Various embodiments of methods for monitoring infection are discussed below. The methods take into account whether an event has occurred that may affect a monitored indicator of infection or a determination as to whether the monitored indicator of infection is predictive of infection. Such methods improve the accuracy of determining whether a monitored indicator is indicative of infection.

Figure 6:
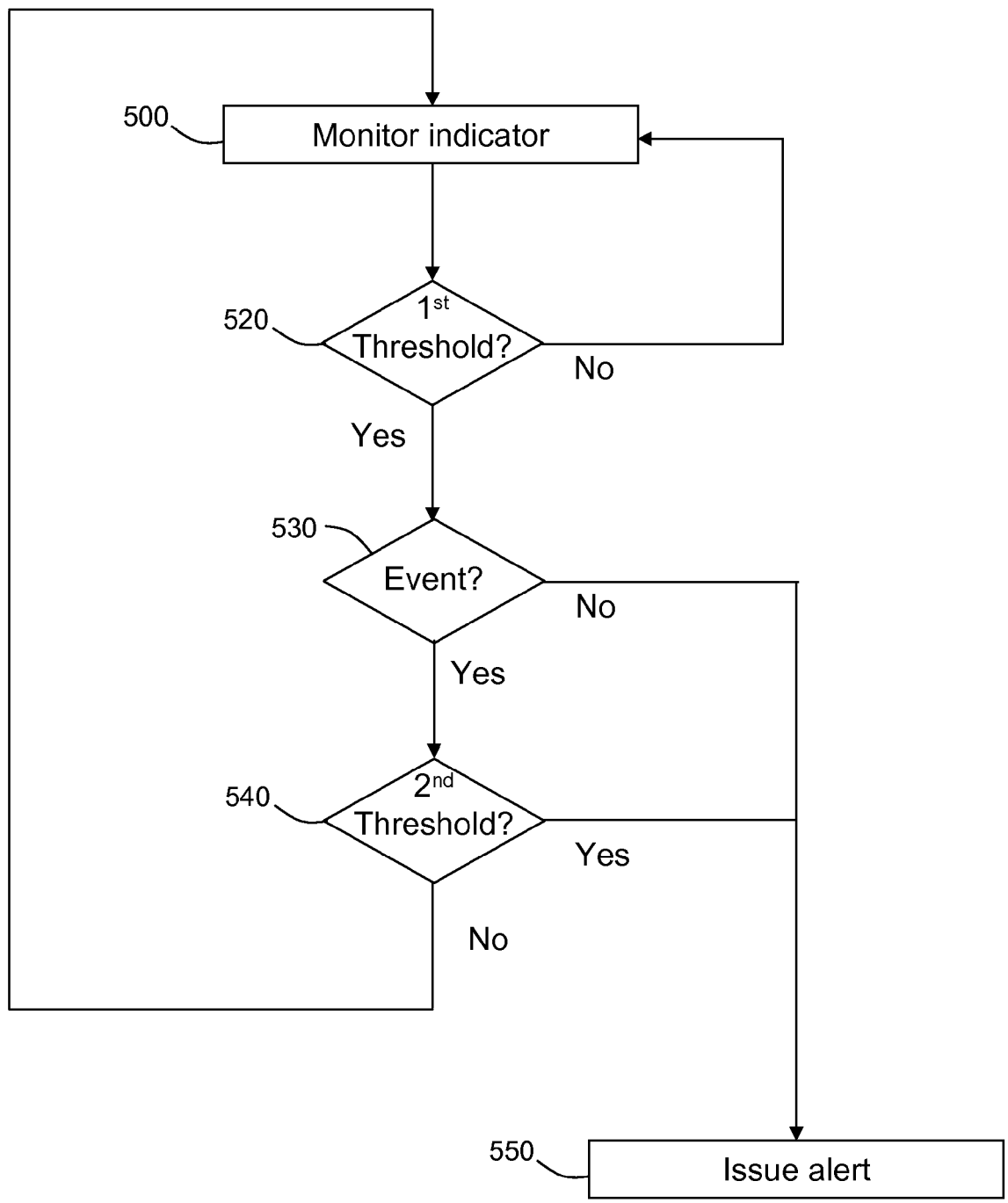
FIG. 6 is a flow diagram of a representative method.
Figure 7:
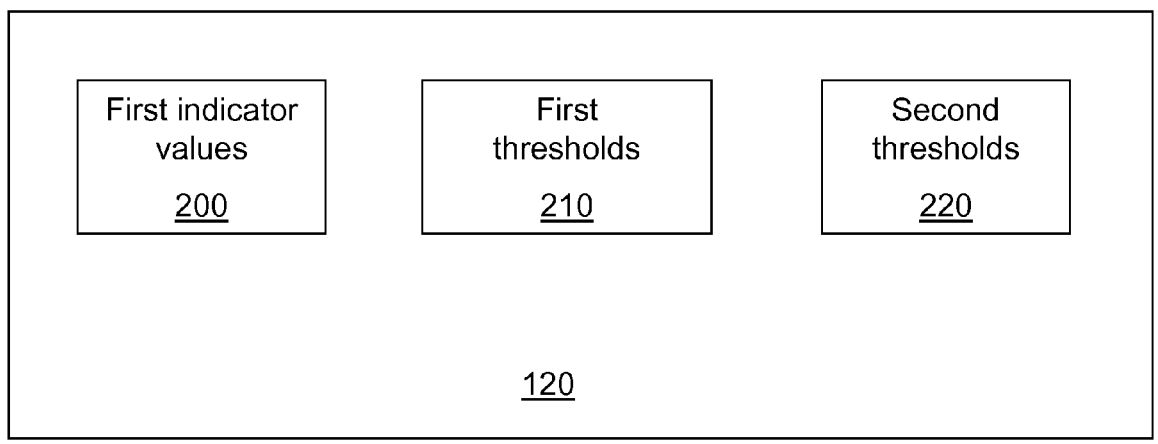
FIG. 7 is a schematic block diagram of representative components of a representative memory of an implantable medical device that may be employed to carryout the method depicted in FIG. 7.

Referring to FIG. 6, a flow diagram of a representative method for monitoring an infection in proximity to an implanted medical device is shown. The method includes monitoring an indicator of infection in proximity to the implanted device (500), which may include, for example, sensor 50, 50' providing information to processor 110 or memory 120. A determination is then made as to whether a value associated with the monitored information has crossed a first threshold indicative of infection (520). For example, processor 110 may compare a value associated with the monitored indicator to a value in a look-up table stored in memory 120 (see, e.g. FIG. 7) to determine whether the first threshold is crossed. If the first threshold is not crossed, the indicator of infection may continue to be monitored (500). If the threshold is crossed, a determination may be made as to whether an event associated with the device has occurred (530). The event is one that may affect a monitored indicator value or a determination as to whether the monitored indicator is indicative of infection. If the event has not occurred within a predetermined time frame or is not occurring, an alert may be issued (550) to warn the patient, a health care provider, or other suitable person that medical action may need to be taken. Issuing the alert (550) may include activating an audible or tactile, e.g. vibration, alarm or providing a visual indication. A visual indication may include, for example, text or an image. The alert may be issued by implanted device 1 or an external device 40, such as a programmer. If the indication is visual, the alert will be presented to the patient or clinician by an external device.

If the event has occurred with in the predetermined timeframe or is occurring (530), a determination may be made as to whether a value associated with the monitored indicator has crossed a second threshold (540). The second threshold takes into account the present or past occurrence of an event. For example, if the event makes it more likely that a value associated with the monitored indicator is predictive of infection; the second threshold may be less then the first threshold. Alternatively, if the event makes it less likely that a value associated with the monitored indicator is predictive of infection; the second threshold may be greater (with respect to the value associated with the indicator) then the first threshold. If the indicator crosses the second threshold, an alert may be issued (550). If the indicator is determined not to cross the second threshold, the indicator may continue to be monitored (500). Of course, while not shown, it will be understood that the indicator may continued to be monitored (500) after an alert is issued (550).

Any event that may affect a monitored indicator of infection or a determination as to whether the monitored indicator is indicative of infection may be taken into account in accordance with the teachings presented herein. By way of example and for purposes of illustration, initiation of recharging or recharging of device 1 will be discussed with temperature being the monitored indicator. If device 1 is being recharged or has recently been recharged, then temperature in proximity of the device 1 may be increased as a result of the recharging. For example, recharging may cause an increase in tissue temperature of 1.5 C in proximity to the device 1. Accordingly, if the first threshold is an absolute number threshold, the second threshold may be 1.5 higher than the first threshold. However, it may be desirable to take into account the timing of the occurrence of the event in relation to the determination as to whether the indicator is indicative of infection is made. For example, a temperature increase associated with recharging a device 1 may occur gradually after initiation of recharging and may dissipate gradually following recharging. Thus, if detection of initiation of a recharge event occurs within seconds of making a determination as to whether temperature is indicative of infection, the weight of the recharge will be discounted relative to, e.g., recharging that has been occurring for an hour or more. To account for time relative to detection of an event, clock 100 may be used to time/date stamp the detection of the event and may be used to facilitate a determination as to how long the event has been occurring. Thus, such information may be taken into account when making a determination as to whether an indicator is indicative of infection. Without taking into account the recharge event, a false positive determination as to the increased temperature being due to an infection may be made.

The amount of heating that is likely to occur during recharging of a device can be calculated in any suitable manner, including those discussed in U.S. patent application Ser. No. 11/737,179, filed on even date herewith, entitled "CONTROLLING TEMPERATURE DURING RECHARGE FOR TREATMENT OF CONDITION", and naming Martin Gerber and John Rondoni as inventors, which application is hereby incorporated herein by reference in its entirety to the extent that it does not conflict with the disclosure presented herein. Effects of various events on various indicators of infections or determinations as to whether the monitored indicator is indicative of infection will be readily identifiable and understood by one of skill in the art.

A determination as to whether a value associated with the monitored indicator of infection crosses a threshold (first or second) may be made in many ways. One example is for processor 110 to compare the monitored value to a value stored in memory 120. For example and referring to FIG. 7, memory 120, according to various embodiments, is shown in more detail. Memory 120 stores information related to indicator of infection values 200, first threshold values 210, and second threshold values 220. Threshold values 210, 220 may be values specified by an external device 40, such as a physician programmer, and may be specifically tailored to a particular patient. Threshold values 220 may be based on the indicator of infection being monitored. Information stored in memory 120 relating to indicator values 200 may be values obtained at a particular point in time, mean or median values, values over time, or the like. Similarly, threshold values 210, 220 may be related to individual values, mean or median values, values over time, or the like. In some embodiments, processor 110 compares an indicator value 200 to a look-up table of threshold values 210, 220 stored in memory 120 to determine whether the monitored indicator is indicative of an infection (520, 540), as appropriate depending on whether an event is determined to have occurred with a predetermined period of time or is occurring (530).

In some embodiments, threshold values 210, 220 are based on information monitored within the patient by device 1. For example, a threshold value 210, 220 may be deviation of 50% or greater, 40% or greater, 30% or greater, 20% or greater, 10% or greater, 5% or greater, etc. from a mean or median value 200, 210 monitored within the patient over a period of time. Processor 110 may compare a value 200 to a calculated threshold value 210, 220. Of course, in such instances, possessor 110 may compare a value 200 to a mean or median value 200 determined over time to determine whether a threshold has been crossed without first storing such threshold value 210, 220 in memory 120. It will be further understood that second threshold values may be calculated by modifying a first threshold value based on the event detected, and perhaps the timing of the detected event.

Additional information regarding infection monitoring and parameters that may be employed is provided in U.S. patent application Ser. No. 11/737,181, entitled "Multi-Parameter Infection Monitoring", filed on even date herewith, naming Martin Gerber and John Rondoni as inventors.

Figure 8:
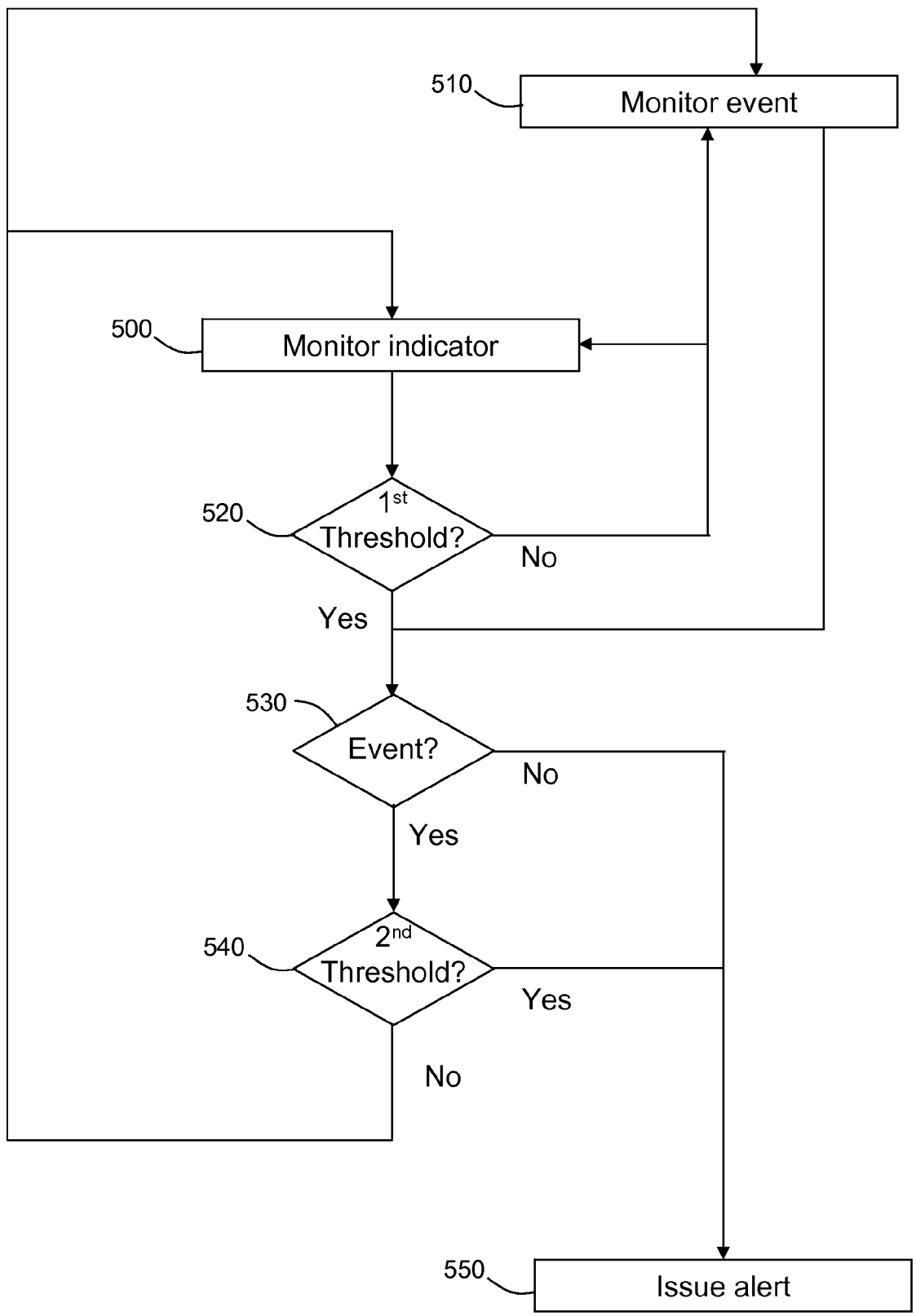
FIGS. 8-9 are flow diagrams of representative methods.

Referring to FIG. 8, a representative method is shown in a flow diagram. The method depicted in FIG. 8 is similar to FIG. 6, but includes monitoring an event (510). A device 1 or component thereof may monitor whether an event is occurring or has occurred. Alternatively or in addition, an external device 40, such as a programmer, may instruct device that an event is occurring or is about to occur. Such instruction may be transmitted via telemetry or other form of wireless communication. In ether case, e.g. monitored or instructed, the event is "detected" by the device 1.

Many forms of input from external device 40 to implanted device 1 may serve as detectable events. For example, input received by the implanted device 1 from an external device 40 that a recharge event has been initiated or is occurring may serve as a detected event. By way of further example, patient input via an external device 40, such as a programmer device, may serve to inform the implanted device 1 of an event. For example, a patient may enter into programmer device that they are exercising or are entering a sauna, events that may affect temperature in proximity to device 1. The patient may enter such information by pressing a button, by selecting an activity from a list presented on a display of the programmer, by typing "exercise", "sauna" or "heat, or the like. The second threshold may then be appropriately modified, and in some cases be set at a level that cannot be crossed for a period of time; e.g., two hours, or until the patient instructs device that the activity has ended. In some embodiments, monitoring of the indicator (500) or determinations as to whether thresholds have been crossed (520, 540) may be halted for a predetermined period time or until the patient instructs device that the activity has ended. In some instances, a patient may provide information prior to an alert being issued (550). In some embodiments, the patient may provide the information after an alert has been issued, e.g. after an alarm has sounded. Receipt of the patient input information may serve to stop the alarm.

Figure 9:
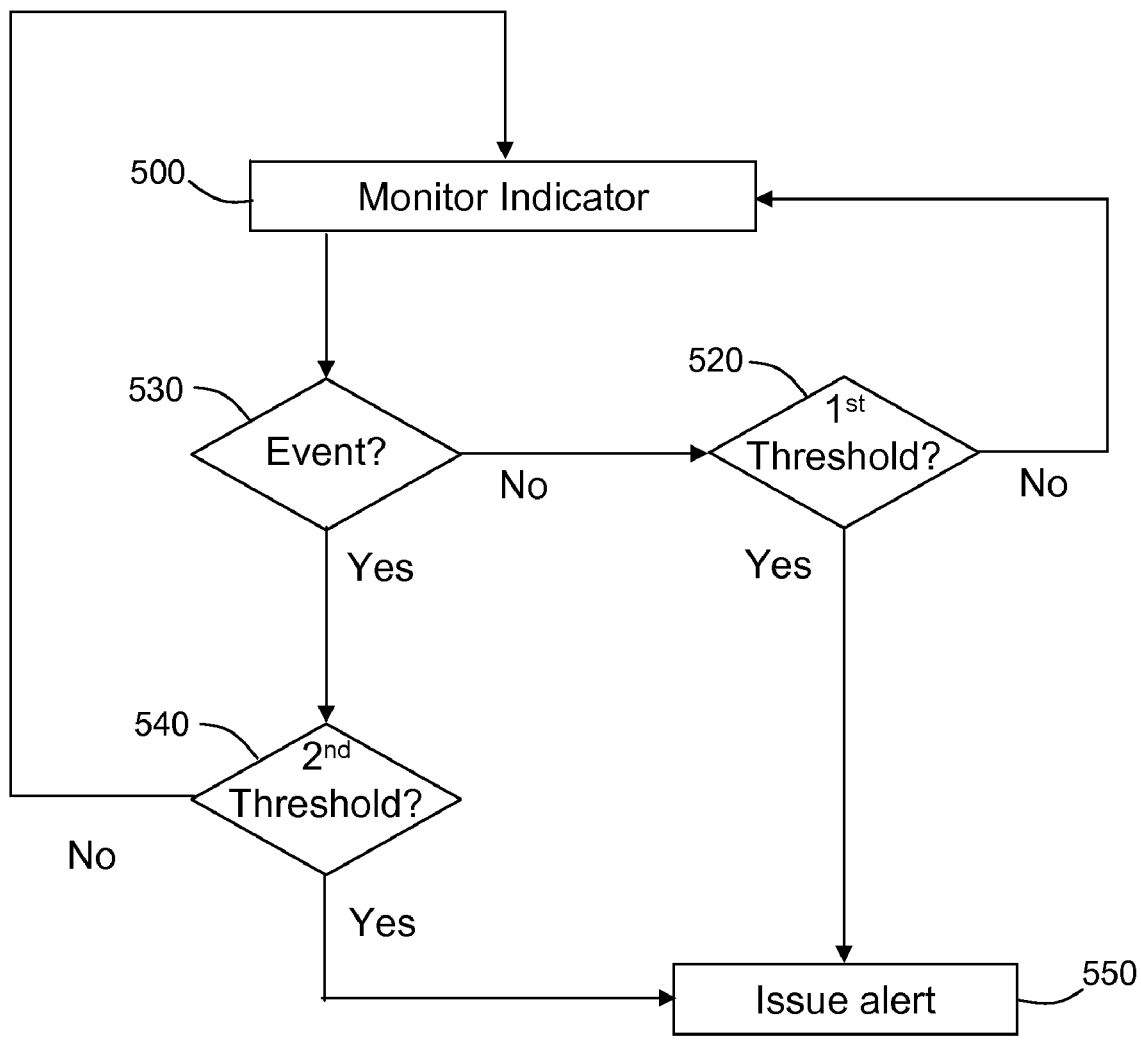

Referring to FIG. 9, a representative method is shown in a flow diagram. The method depicted in FIG. 9 is similar to FIG. 6, but shows a determination being made as to whether an event occurs (530) prior to determining whether the monitored indicator crosses a first threshold (520). Of course it will be understood that the methods described herein may be carried out in any suitable order. The order in which various portions of the methods may be modified according to various factors, such as whether more than one device (for example, implanted device 1 and external device 40) are used to carry out the method, whether power consumption by implanted device is a concern, e.g. minimizing numbers of calculations performed, or the like.

If power consumption by implanted device is a concern, monitoring of indicators of infection or events, and determinations as to whether an indicator is predictive of infection may be preformed in discrete time intervals rather than continuously. Additional information regarding power savings associated with infection monitoring is provided in (i) U.S. patent application Ser. No. 11/737,169, filed on even date therewith, entitled "EVENT TRIGGERED INFECTION MONITORING", naming Martin Gerber and John Rondoni as inventors, and (ii) U.S. patent application Ser. No. 11/737,170, filed on even date herewith, entitled "INFECTION MONITORING", naming Martin Gerber and John Rondoni as inventors, which applications are hereby incorporated herein by reference in their respective entireties to the extent that they do not conflict with the disclosure presented herein.

One of skill in the art will understand that components or steps described herein regarding a given embodiment or set of embodiments may readily be omitted, substituted, or added from, with, or to components or steps of other embodiments or sets of embodiments, as appropriate or desirable.

It will be further understood that a computer readable medium containing instructions that when implemented cause an implantable medical device (or system including an implantable medical device) to perform the methods described herein are contemplated. In an embodiment the computer readable medium contains instructions that when implemented cause an implantable medical device to (i) monitor an indicator of infection in proximity to the device; (ii) determine whether a value associated with the indicator of infection crosses a first threshold indicative of infection; (iii) detect an event associated with the device, the event capable of affecting the indicator of infection; (iv) determine whether the value associated with the indicator of infection crossed a second threshold indicative of infection if the event is detected; and (v) provide an alert either if the first threshold is crosses and the event is not detected or if the second threshold is crossed and the event is detected.

Devices including the computer readable medium are also contemplated. For example, an implantable medical device may include electronics capable executing computer readable instructions and capable of detecting an event associated with the device. The event is capable of affecting an indicator of infection. The device may further include a sensor operably coupled to the electronics. The sensor is capable of detecting the indicator of infection. The device may also include an alarm capable of providing a sensory cue. In addition the device may include a computer readable medium containing instructions that when implemented by the electronics cause the device to (i) determine whether a value associated with the indicator of infection crosses a first threshold indicative of infection; (ii) determine whether the value associated with the indicator of infection crosses a second threshold indicative of infection if the event is detected; and (iii) activate the alarm either if the first threshold is crosses and the event is not detected or if the second threshold is crossed and the event is detected.

In addition, the principles of the methods, systems and devices described herein may be used for detecting various other potential adverse health issues associated with an implantable medical device. For example, temperature, pH, impedance, and various indicators of infection may also be used to determine whether a hematoma, edema, or seroma is present in proximity to an implanted device. Accordingly, monitoring of such other potential adverse health issues is within the scope of the present disclosure.

Additional information regarding infection monitoring that may provide additional insight into the teachings provided herein include is provided in U.S. patent application Ser. No. 11/737,173, filed on even date herewith, entitled "Infection Monitoring", naming Martin Gerber and John Rondoni as inventors, which patent application is hereby incorporated herein by reference in its entirety to the extent that it does not conflict with the disclosure presented herein.

Thus, embodiments of REFINED INFECTION MONITORING are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for monitoring an infection in proximity to an implanted medical device, comprising:
    monitoring, via the implantable medical device, an indicator of infection in proximity to the device;
    determining whether a value associated with the indicator of infection crosses a first threshold indicative of infection;
    determining if an event associated with the device that is capable of affecting the indicator of infection has occurred, wherein determining whether the event associated with the device has occurred, comprises detecting a recharging event;
    determining whether the value associated with the indicator of infection crosses a second threshold indicative of infection if the event has occurred; and
    issuing an alert if:
        (i) the first threshold is crossed and the event has not occurred, or
        (ii) the second threshold is crossed and the event has occurred.

2. The method of claim 1 wherein monitoring the indicator of infection comprises monitoring temperature.

3. The method of claim 2, wherein the second threshold includes a higher temperature parameter than the first threshold.

4. A computer readable medium containing instructions that when implemented cause an implantable medical device to (i) monitor an indicator of infection in proximity to the device; (ii) determine whether a value associated with the indicator of infection crosses a first threshold indicative of infection; (iii) determine if an event associated with the device has occurred, the event capable of affecting the indicator of infection, wherein the event is a recharging event; (iv) determine whether the value associated with the indicator of infection crossed a second threshold indicative of infection if the event has occurred; and (v) provide an alert either if the first threshold is crossed and the event has not occurred or if the second threshold is crossed and the event has occurred.

5. An implantable medical device comprising:

electronics capable of executing computer readable instructions and capable of detecting an event associated with the device, the event capable of affecting an indicator of infection;

a sensor operably coupled to the electronics, the sensor capable of detecting the indicator of infection;

an alarm capable of providing a sensory cue; and a computer readable medium containing instructions that when implemented by the electronics cause the device to (i) determine whether a value associated with the indicator of infection crosses a first threshold indicative of infection, wherein the event is a recharging event; (ii) determine whether the value associated with the indicator of infection crosses a second threshold indicative of infection if the event is detected; and (iii) activate the alarm either if the first threshold is crossed and the event is not detected or if the second threshold is crossed and the event is detected.

6. The device of claim 5, wherein the sensor is a temperature sensor.

* * * * *